(12) United States Patent
Mannheimer et al.

(10) Patent No.: US 8,000,760 B2
(45) Date of Patent: Aug. 16, 2011

(54) METHOD AND CIRCUIT FOR STORING AND PROVIDING HISTORICAL PHYSIOLOGICAL DATA

(75) Inventors: Paul D. Mannheimer, Danville, CA (US); Michael E. Fein, Mountain View, CA (US); Marcia Fein, legal representative, Mountain View, CA (US)

(73) Assignee: Mallinckrodt Inc., Hazelwood, MO (US)

( * ) Notice: Subject to any disclaimer, the term of this patent is extended or adjusted under 35 U.S.C. 154(b) by 1432 days.

(21) Appl. No.: 11/445,110

(22) Filed: Jun. 1, 2006

(65) Prior Publication Data
US 2007/0043273 A1 Feb. 22, 2007

Related U.S. Application Data

(60) Continuation of application No. 10/452,806, filed on May 30, 2003, which is a division of application No. 09/943,899, filed on Aug. 30, 2001, now Pat. No. 6,606,510.

(60) Provisional application No. 60/229,616, filed on Aug. 31, 2000.

(51) Int. Cl.
*A61B 5/1455* (2006.01)
(52) U.S. Cl. ........................ 600/323; 600/310
(58) Field of Classification Search .................. 600/323, 600/310, 322
See application file for complete search history.

(56) References Cited

U.S. PATENT DOCUMENTS

| | | | |
|---|---|---|---|
| 3,720,199 A | 3/1973 | Rishton et al. |
| 3,790,910 A | 2/1974 | McCormack |
| 3,797,479 A | 3/1974 | Graham |
| 4,041,935 A | 8/1977 | Garbe |
| 4,210,155 A | 7/1980 | Grimes |
| 4,303,984 A | 12/1981 | Houvig |
| 4,446,715 A | 5/1984 | Bailey |
| 4,621,643 A | 11/1986 | New, Jr. et al. |
| 4,653,498 A | 3/1987 | New, Jr. et al. |
| 4,684,245 A | 8/1987 | Goldring |
| 4,684,246 A | 8/1987 | Downing |
| 4,700,708 A | 10/1987 | New, Jr. et al. |
| 4,714,080 A | 12/1987 | Edgar et al. |
| 4,717,080 A | 1/1988 | Sauer |
| 4,734,873 A | 3/1988 | Malloy et al. |
| 4,845,649 A | 7/1989 | Eckardt et al. |
| 4,845,873 A | 7/1989 | Hazlett |
| 4,858,615 A | 8/1989 | Meinema |
| 4,862,872 A | 9/1989 | Yabe et al. |
| 4,913,150 A | 4/1990 | Cheung et al. |
| 4,942,877 A | 7/1990 | Sakai et al. |
| 5,007,423 A | 4/1991 | Branstetter |
| 5,008,843 A | 4/1991 | Poelsler et al. |
| 5,016,198 A | 5/1991 | Schreiber |
| 5,025,791 A | 6/1991 | Niwa |
| 5,058,588 A | 10/1991 | Kaestle |

(Continued)

FOREIGN PATENT DOCUMENTS

DE 3028061 9/1982

(Continued)

*Primary Examiner* — Eric F Winakur
(74) *Attorney, Agent, or Firm* — Fletcher Yoder

(57) ABSTRACT

Embodiments of the present invention include systems and methods that relate to pulse oximetry. Specifically, one embodiment includes an oximeter sensor comprising a light emitting element configured to emit light, a light detector configured to detect the light, and a memory storing an optical shunting measurement for the oximeter sensor.

8 Claims, 3 Drawing Sheets

U.S. PATENT DOCUMENTS

| | | | |
|---|---|---|---|
| 5,070,732 A | 12/1991 | Duncan et al. | |
| 5,162,725 A | 11/1992 | Hodson et al. | |
| 5,226,417 A | 7/1993 | Swedlow et al. | |
| 5,246,003 A | 9/1993 | DeLonzor | |
| 5,259,381 A | 11/1993 | Cheung et al. | |
| 5,329,931 A | 7/1994 | Clauson et al. | |
| 5,341,291 A | 8/1994 | Roizen et al. | |
| 5,347,476 A | 9/1994 | McBean, Sr. | |
| 5,360,005 A | 11/1994 | Wilk | |
| 5,365,462 A | 11/1994 | McBean, Sr. | |
| 5,368,026 A | 11/1994 | Swedlow et al. | |
| 5,371,128 A | 12/1994 | Ulman et al. | |
| 5,372,141 A | 12/1994 | Gallup et al. | |
| 5,385,144 A | 1/1995 | Yamanishi et al. | |
| 5,400,267 A * | 3/1995 | Denen et al. | 128/908 |
| 5,425,375 A | 6/1995 | Chin | |
| 5,429,129 A | 7/1995 | Lovejoy et al. | |
| 5,431,170 A | 7/1995 | Mathews | |
| 5,443,801 A | 8/1995 | Langford | |
| 5,448,991 A | 9/1995 | Polson et al. | |
| 5,513,646 A | 5/1996 | Lehrman et al. | |
| 5,528,519 A | 6/1996 | Ohkura et al. | |
| 5,627,531 A | 5/1997 | Posso et al. | |
| 5,645,059 A | 7/1997 | Fein et al. | |
| 5,645,060 A | 7/1997 | Yorkey | |
| 5,645,069 A | 7/1997 | Lee | |
| 5,660,163 A | 8/1997 | Schulman et al. | |
| 5,660,176 A | 8/1997 | Iliff | |
| 5,678,448 A | 10/1997 | Fullen et al. | |
| 5,682,877 A | 11/1997 | Mondry | |
| 5,718,235 A | 2/1998 | Golosarsky et al. | |
| 5,720,293 A | 2/1998 | Quinn et al. | |
| 5,730,124 A | 3/1998 | Yamauchi | |
| 5,758,644 A | 6/1998 | Diab | |
| 5,800,350 A | 9/1998 | Coppleson et al. | |
| 5,818,583 A | 10/1998 | Sevick-Muraca et al. | |
| 5,830,121 A | 11/1998 | Enomoto et al. | |
| 5,830,135 A | 11/1998 | Bosque | |
| 5,855,609 A | 1/1999 | Knapp | |
| 5,865,736 A | 2/1999 | Baker, Jr. et al. | |
| 5,954,644 A | 9/1999 | Dettling et al. | |
| 5,961,446 A | 10/1999 | Beller | |
| 5,964,701 A | 10/1999 | Asada et al. | |
| 5,987,343 A | 11/1999 | Kinast | |
| 5,995,859 A | 11/1999 | Takahashi | |
| 6,004,276 A | 12/1999 | Wright et al. | |
| 6,018,673 A | 1/2000 | Chin et al. | |
| 6,023,541 A | 2/2000 | Merchant et al. | |
| 6,044,283 A | 3/2000 | Fein et al. | |
| 6,095,984 A | 8/2000 | Amano et al. | |
| 6,104,938 A | 8/2000 | Huiku et al. | |
| 6,122,536 A | 9/2000 | Sun et al. | |
| 6,241,679 B1 | 6/2001 | Curran | |
| 6,298,252 B1 | 10/2001 | Kovach et al. | |
| 6,298,255 B1 | 10/2001 | Cordero | |
| 6,308,089 B1 | 10/2001 | von der Ruhr et al. | |
| 6,330,464 B1 * | 12/2001 | Colvin et al. | 600/316 |
| 6,356,774 B1 | 3/2002 | Bernstein et al. | |
| 6,360,114 B1 | 3/2002 | Diab et al. | |
| 6,374,129 B1 | 4/2002 | Chin et al. | |
| 6,377,829 B1 | 4/2002 | Al-Ali | |
| 6,405,087 B1 | 6/2002 | Snell | |
| 6,463,310 B1 | 10/2002 | Swedlow et al. | |
| 6,466,808 B1 | 10/2002 | Chin | |
| 6,591,123 B2 | 7/2003 | Fein | |
| 6,608,934 B2 | 8/2003 | Scheirer et al. | |
| 6,708,049 B1 | 3/2004 | Berson et al. | |
| 6,801,797 B2 | 10/2004 | Mannheimer et al. | |
| 6,845,256 B2 | 1/2005 | Chin et al. | |
| 6,934,571 B2 | 8/2005 | Wiesmann et al. | |
| 6,950,687 B2 | 9/2005 | Al-Ali | |
| 6,979,812 B2 | 12/2005 | Al-Ali | |
| 6,988,056 B2 | 1/2006 | Cook | |
| 7,047,055 B2 * | 5/2006 | Boas et al. | 600/338 |
| 7,048,687 B1 | 5/2006 | Reuss et al. | |
| 7,187,441 B1 | 3/2007 | Sevick-Muraca et al. | |
| 7,260,425 B2 | 8/2007 | Chin et al. | |
| 7,272,425 B2 | 9/2007 | Al-Ali | |
| 7,457,652 B2 | 11/2008 | Porges et al. | |
| 2002/0103423 A1 | 8/2002 | Chin et al. | |
| 2003/0135099 A1 | 7/2003 | Al-Ali | |
| 2005/0070773 A1 | 3/2005 | Chin et al. | |
| 2005/0070775 A1 | 3/2005 | Chin et al. | |
| 2005/0165323 A1 | 7/2005 | Montgomery et al. | |
| 2006/0030763 A1 | 2/2006 | Mannheimer et al. | |
| 2006/0030764 A1 | 2/2006 | Porges et al. | |
| 2006/0161054 A1 | 7/2006 | Reuss et al. | |
| 2006/0224059 A1 | 10/2006 | Swedlow et al. | |
| 2006/0259925 A1 | 11/2006 | Lemmons et al. | |
| 2007/0156034 A1 | 7/2007 | Al-Ali | |
| 2007/0208235 A1 | 9/2007 | Besson et al. | |
| 2007/0299328 A1 | 12/2007 | Chin et al. | |
| 2008/0287757 A1 | 11/2008 | Berson et al. | |

FOREIGN PATENT DOCUMENTS

| | | |
|---|---|---|
| EP | 0 949 506 A2 | 10/1999 |
| GB | 2247838 | 3/1992 |
| JP | 3939782 B2 | 7/2007 |
| JP | 4038280 B2 | 1/2008 |
| WO | WO89/09023 | 10/1989 |
| WO | WO 93/06775 | 4/1993 |
| WO | WO 93/06776 | 4/1993 |
| WO | WO93/06778 | 4/1993 |
| WO | WO 97/29678 | 8/1997 |
| WO | WO 97/47233 | 12/1997 |

* cited by examiner

METHOD AND CIRCUIT FOR STORING AND PROVIDING HISTORICAL PHYSIOLOGICAL DATA

This application is a continuation of U.S. patent application Ser. No. 10/452,806, filed May 30, 2003, which is a divisional application of U.S. patent application Ser. No. 09/943,899, filed Aug. 30, 2001, which issued as U.S. Pat. No. 6,606,510 and claims the benefit of U.S. Provisional Application Ser. No. 60/299,616, filed Aug. 31, 2000, all of which are incorporated herein by reference.

BACKGROUND

Pulse oximetry is typically used to measure various blood flow characteristics including, but not limited to, the blood oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor that passes light through a portion of a patient's blood perfused tissue and photo-electrically senses the absorption and scattering of light in such tissue. The amount of light absorbed is then used to estimate the amount of blood constituent in the tissue. The "pulse" in pulse oximetry comes from the time varying amount of arterial blood in the tissue during the cardiac cycle. The signal processed from the sensed optical signal is a familiar plethysmographic waveform due to cycling light attenuation.

To estimate blood oxygen saturation of a patient, conventional two-wavelength pulse oximeters emit light from two light emitting diodes (LEDs) into a pulsatile tissue bed and collect the transmitted light with a photodiode (or photo-detector) positioned on an opposite surface (i.e., for transmission pulse oximetry) or an adjacent surface (i.e., for reflectance pulse oximetry). One of the two LEDs' primary wavelength is selected at a point in the electromagnetic spectrum where the absorption of oxyhemoglobin ($HbO_2$) differs from the absorption of reduced hemoglobin (Hb). The second of the two LEDs' wavelength is selected at a different point in the spectrum where the absorption of Hb and $HbO_2$ differs from those at the first wavelength. Commercial pulse oximeters typically utilize one wavelength in the near red part of the visible spectrum near 660 nanometers (nm) and one in the near infrared (IR) part of the spectrum in the range of 880-940 nm. The amount of transmitted light passed through the tissue will vary in accordance with the changing amount of blood constituent in the tissue and the related light absorption.

An encoding mechanism is shown in U.S. Pat. No. 4,700,708, the disclosure of which is incorporated herein by reference. This mechanism relates to an optical oximeter probe which uses a pair of light emitting diodes (LEDs) to direct light through blood perfused tissue, with a detector picking up light which has not been absorbed by the tissue. The operation depends upon knowing the wavelength of the LEDs. Since the wavelength of LEDs can vary, a coding resistor is placed in the probe with the value of the resistor corresponding to the actual wavelength of at least one of the LEDs. When the oximeter instrument is turned on, it first applies a current to the coding resistor and measures the voltage to determine the value of the resistor and thus the value of the wavelength of the LED in the probe.

Oxygen saturation can be estimated using various techniques. In one common technique, the photo-current generated by the photo-detector is conditioned and processed to determine the modulation ratio of the red to infrared signals. This modulation ratio has been observed to correlate well to arterial oxygen saturation. The pulse oximeters and sensors are empirically calibrated by measuring the modulation ratio over a range of in vivo measured arterial oxygen saturations ($SaO_2$) on a set of patients, healthy volunteers, or animals. The observed correlation is used in an inverse manner to estimate blood oxygen saturation ($SpO_2$) based on the measured value of modulation ratios of a patient. The estimation of oxygen saturation using modulation ratios is described in U.S. Pat. No. 5,853,364, entitled "METHOD AND APPARATUS FOR ESTIMATING PHYSIOLOGICAL PARAMETERS USING MODEL-BASED ADAPTIVE FILTERING", issued Dec. 29, 1998, and U.S. Pat. No. 4,911,167, entitled "METHOD AND APPARATUS FOR DETECTING OPTICAL PULSES", issued Mar. 27, 1990. The relationship between oxygen saturation and modulation ratio is further described in U.S. Pat. No. 5,645,059, entitled "MEDICAL SENSOR WITH MODULATED ENCODING SCHEME," issued Jul. 8, 1997. All three patents are assigned to the assignee of the present invention and incorporated herein by reference.

Nellcor U.S. Pat. No. 5,645,059, the disclosure of which is hereby incorporated herein by reference, teaches coding information in sensor memory used to provide pulse modulated signal, to indicate the type of sensor (finger, nose), the wavelength of a second LED, the number of LEDs, the numerical correction terms to the standard curves, and an identifier of the manufacturer.

The LEDs and photo-detector are typically housed in a reusable or disposable oximeter sensor that couples to the pulse oximeter electronics and the display unit (hereinafter referred to as the monitor). The sensors are often connected to patients for long periods of time. Conventionally, historical physiological data for the patient is collected, if at all, by the monitor coupled to the sensor. The historical data can be valuable to a clinician or medical personnel for diagnostic and monitoring purposes. Patients are often moved to various locations during treatment. For example, a patient may be picked up in an ambulance, delivered to an emergency room, moved to an operating room, transferred to a surgical recovery room, transferred to an intensive care unit, and then moved to a nursing floor or other locations. Thus, the patient may be moved between various locations within the same hospital, or between different hospitals. In many instances, the sensor employed to monitor the condition of the patient is adhesive in its attachment and remains with the patient. The monitors, however, are typically local to particular locations within a facility or vehicle. The sensor is normally disconnected from the monitor at a departure site and reconnected to another monitor at a destination site. Consequently, any patient related data (e.g., historical physiological data) collected by the monitor at the departure site is normally unavailable to the clinician attending the patient at the destination site.

DETAILED DESCRIPTION

Figure 1:
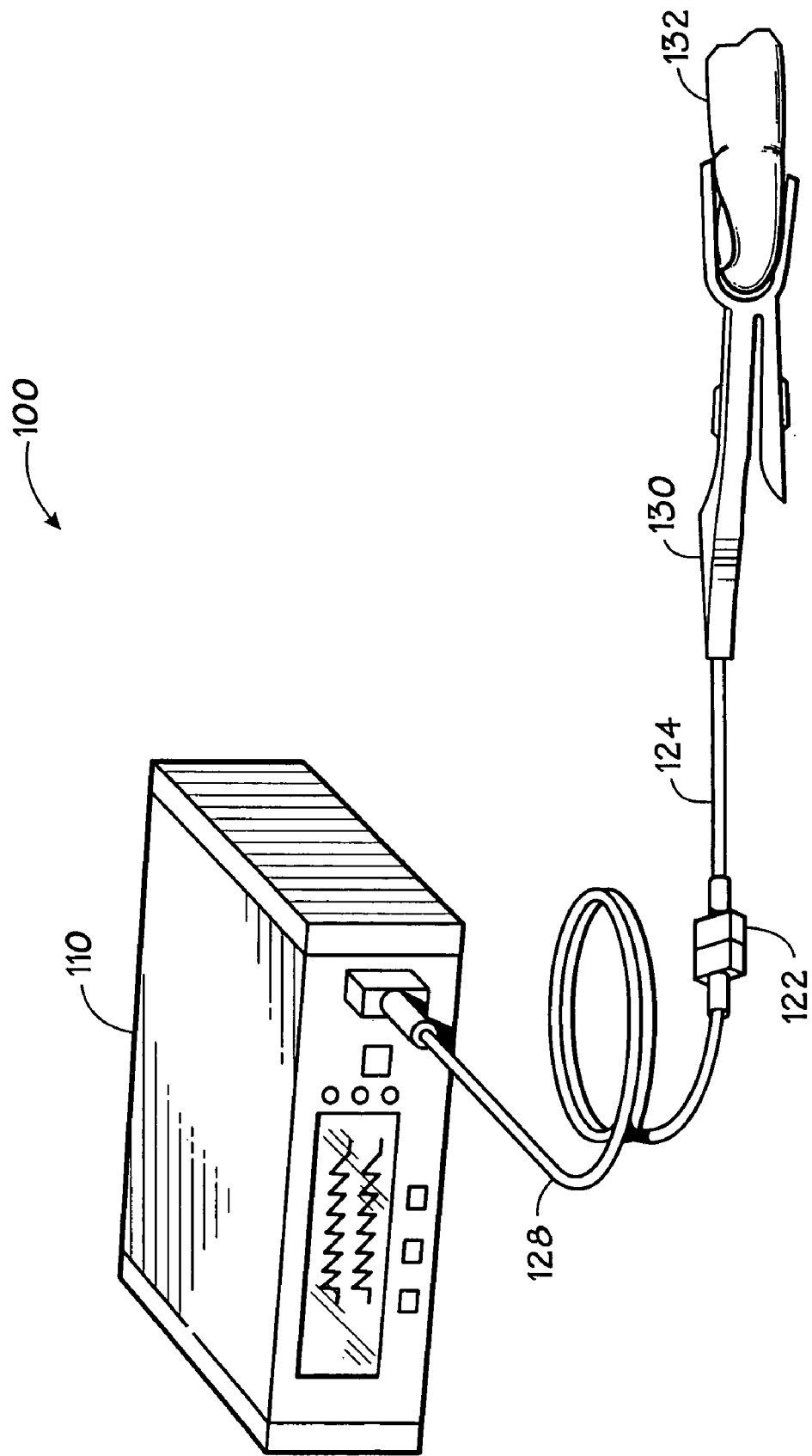
FIG. 1 shows a perspective view of an exemplary embodiment of an oxygen measurement system.

The present techniques relate to physiological monitoring instruments and, in particular, sensors that include a mechanism for storing and providing to a monitor historical physiological data such as blood oxygen saturation data. Embodiments of the present invention include pulse oximetry sensors that include coded information relating to patients.

The present techniques provide a memory chip for use in an oximeter sensor, or an associated adapter or connector circuit to provide enhanced capabilities for the oximeter sensor. The techniques provide a mechanism for storing and providing patient related data such as patient trending data, a patient ID or historical physiological data (e.g., blood oxygen saturation data for a patient).

In addition to providing unique data to store in such a memory, the present techniques include unique uses of the data stored in such a memory. In a specific embodiment, the patient related data (e.g., historical physiological data) is stored in a storage medium that "travels" with the patient and is accessible wherever the patient is moved. This is achieved by storing the data within a sensor assembly, (e.g., within the sensor itself, a connector plug, a connector cable, or an interconnection module). At the destination site, a monitor or a device capable of interfacing with the sensor assembly electronics can retrieve and display the data. The stored data allows a clinician or medical personnel at the destination site to assess the condition of the patient for the entire time that the patient has been previously monitored. The techniques can be used to store and provide various types of physiological data including, but not limited to, patient trending data, a patient ID, blood oxygen saturation, heart rate, blood pressure, and temperature data.

A specific embodiment provides a pulse oximeter sensor that includes a number of light sources, at least one photo-detector, and a memory circuit associated with the sensor. The light sources are selected to operate at different wavelengths. The photo-detector receives light emitted by the plurality of light sources. The memory circuit stores patient related data. For example, the memory circuit stores physiological data derived from the detected light and sent to the circuit by an oximeter monitor, and the circuit then provides the data later when requested by a monitor. The physiological data is indicative of a physiological condition of a patient being monitored by the sensor.

Another specific embodiment provides a method for storing patient related data (e.g., physiological data). The method detects, via a sensor, at least one signal indicative of a physiological condition, and conditions the detected signal to generate data samples. The data samples are processed to generate the physiological data, wherein the physiological data describes the physiological condition. The physiological data is stored within a memory associated with the sensor. The physiological data can be coded and compressed before storage to the memory. Other types of patient data (e.g., patient ID) are stored on the memory in other embodiments.

Part I

FIG. 1 shows a perspective view of an exemplary embodiment of a physiological measurement system 100. System 100 includes a monitor 110. Monitor 110 couples via an electrical cable 128 to a sensor 130 that is applied to a patient 132. Sensor 130 includes a sensor cable 124 and a sensor connecting plug 122. Sensor 130 may include light sources (e.g., LEDs) and a photo-detector along with suitable components to couple the electro-optical components to electrical cable 128. Sensor 130 is shown in FIG. 1 as a clip-on sensor. However, present embodiments can be applied to many sensor implementations, including those attached to a patient by adhesive and other attachment means. In a specific embodiment, monitor 110 is a pulse oximeter and sensor 130 is a pulse oximeter sensor. However, the sensor may include a temperature, heart rate, blood pressure, or other type of physiological sensor.

In an exemplary embodiment, for estimating blood oxygen saturation, light from light sources at two or more wavelengths (e.g., red and infrared) is transmitted through a patient's blood perfused tissues (e.g., in a finger) and detected by a photo-detector. The selection of the wavelengths is based on a number of factors. Such factors include the absorption characteristics of the patient and transmission medium. The light sources and photo-detector are typically housed within a sensor that couples to the monitor (e.g., the pulse oximeter). The detected optical signal is then provided to the monitor for processing.

Figure 2:
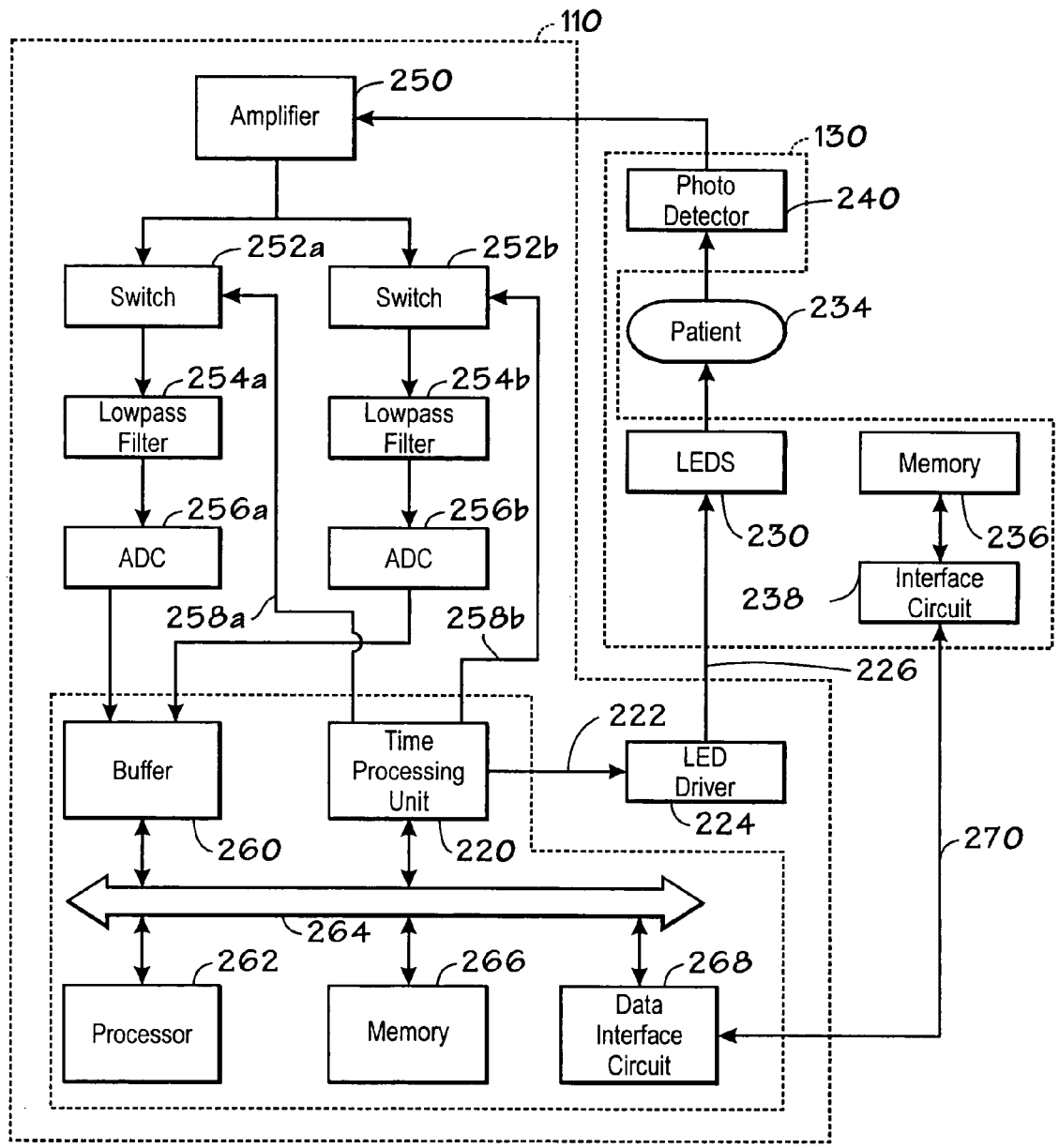
FIG. 2 shows a block diagram of an exemplary embodiment of an oxygen monitor and sensor.

FIG. 2 shows a block diagram of an embodiment of monitor 110 and sensor 130. Within monitor 110, a time processing unit (TPU) 220 provides control signals 222 to an LED driver 224 that, via data line(s) 226, alternately activates LEDs 230 within sensor 130. Depending on the particular implementation, LEDs 230 include two or more LEDs and LED driver 224 provides the drive signals for the LEDs. When activated, the light from LEDs 230 passes through a medium (e.g., air or a fiber optic cable, depending on the implementation) into a patient's tissues 234. After being transmitted through or reflected from the tissues, the light is received by a photo-detector 240 via another medium (e.g., air or another fiber optic cable). Photo-detector 240 converts the received light into a photo-current, which is then provided to an amplifier 250 that amplifies the photo-current.

As shown in FIG. 2, the amplified signal from amplifier 250 is provided to circuitry for two different channels, one channel for each of the red and infrared wavelengths. For a three-wavelength implementation, circuitry is provided for three channels. Each channel circuitry includes an analog switch 252 coupled in series with a low pass filter 254 that is further coupled in series with an analog-to-digital converter (ADC) 256. Control lines 258 from time processing unit 220 select the sampled data from the channel corresponding to the LED being activated. Specifically, the sampled data from ADC 256a is selected when the red LED is activated and the sampled data from ADC 256b is selected when the infrared LED is activated. The sampled data from ADCs 256 is provided to a buffer 260 that stores the data for further processing. In an implementation, as buffer 260 periodically fills up, a processor 262 coupled to a bus 264 directs the transfer of the data from buffer 260 into a memory 266. The monitor implementation shown in FIG. 2 is one of many implementations. The present techniques can be adapted for application in various monitor implementations.

The sensor 130 may include circuitry that stores historical physiological data and provides the data when requested. As shown in FIG. 2, sensor 130 includes a memory 236 coupled to an interface circuit 238. Interface circuit 238 provides signal conditioning, and can also provide other functions such as address decoding, and so on. Interface circuit 238 couples via a bus 270 to a data interface circuit 268 within monitor 110. Through interface circuits 238 and 268, physiological data is transferred between monitor 110 and sensor 130.

In an embodiment, to enhance compatibility of the present sensor with conventional sensors and conventional monitors, bus 270 is implemented using new signal lines (i.e., not using or sharing the existing signal lines of conventional sensors). Bus 270 can be implemented as a serial bus, a parallel bus, or other bus architectures. With this implementation, when sensor 130 is plugged into a monitor not capable of supporting its features, the signals on interface circuit 238 are simply ignored by the monitor, or alternatively not requested by the monitor.

In another embodiment, interface circuits 238 and 268 interact via signal line(s) or wire(s) existing in conventional sensors and monitors. For example, interface circuits 238 and 268 can couple via data line(s) 226 and time multiplex with the LED drive signals from LED driver 224.

Time processing unit 220, buffer 260, processor 262, memory 266, and data interface circuit 268 can be implemented in various manners. For example, these elements can be implemented within a single integrated circuit, such as a DMC68HC 16 micro-controller from Motorola. These elements can also be implemented within an application specific integrated circuit (ASIC), a digital signal processor, a micro-controller, or other circuits.

In one embodiment, patient-specific data such as trending data or patient monitoring parameters can be actively stored in the memory 236 (e.g., a memory chip). As the patient and sensor travel from ward-to-ward of the hospital, and consequently plug into different oximeters, the patient-specific data can be read from memory 236 of the patient's dedicated sensor and displayed on a display screen for viewing or used by the oximeter monitor for other purposes. Memory 236 may, for example, be implemented as a random access memory (RAM), a FLASH memory, a programmable read only memory (PROM), an electrically erasable PROM, a similar programmable and/or erasable memory, any kind of erasable memory, a write once memory, or other memory technologies capable of write operations. Examples of patient specific data that can be stored in memory 236 are now discussed.

Patient trending data regarding the history of a patient's blood oxygen saturation (SpO₂) level, pulse rate, pulse amplitude, perfusion data, and other patient data over a period of time can be recorded in memory 236. The oximeter monitor can continuously or periodically store a patient's current trend data into memory 236 to maintain a historical data for the patient. The memory can be erased and overwritten multiple times. For example, the patient trend data can be erased from memory 236 each time a sensor is used on a new patient (e.g., each time the oximeter monitor is turned off or when user input to the monitor indicates a new patient). This memory characteristic may be advantageous, for example, for nondisposable sensors that may be used multiple times on multiple patients. Specific examples of memory devices that can be erased and overwritten are Flash, EEPROM, battery backed RAM, and other technologies. Alternatively, the data encoded into memory 236 can be permanent and non-erasable. In a specific embodiment, to preserve the historical data and prevent accidental erasure, the sensor memory can be written only once. This memory characteristic also prevents erasure of the data during sensor operation. Further details of a Method and Circuit for Storing and Providing Historical Physiological Data are discussed in U.S. patent application Ser. No. 09/520,104 to Swedlow et al., filed Mar. 7, 2000, which is incorporated by reference herein in its entirety.

As another example, the lowest and/or highest blood oxygen saturation level, pulse rate, pulse amplitude value, temperature data, blood pressure, perfusion data, or any other patient data during the monitored time may be stored in memory 236 by the oximeter monitor. If desired, the lowest/highest values of these patient parameters over a past specified monitoring time (e.g., 2 hours, 1 day, etc.) may be recorded in memory 236.

Expected ranges for patient parameters (such as pulse rate, pulse amplitude, and blood oxygen saturation level) that are specific to a particular patient may also be recorded in memory 236 by a clinician. This can be a desirable feature, because the expected patient trending data can vary significantly for each patient. The oximeter monitor can compare the expected range for the patient stored in memory 236 with the monitored patient trending data to determine if the patient's pulse and blood oxygen levels are within the expected range for that patient. If the monitored patient parameter varies outside the patient-specific range recorded in memory 236, a warning message may be displayed on the oximeter monitor or an alarm signal may be sounded. If desired, any variations in the monitored patient parameters from the expected ranges may be recorded in memory 236 along with a time stamp.

If desired, portions of a patient's medical chart and/or past medical history can be digitally encoded and stored in memory 236 (if sufficient memory space is available) so that this information is maintained with the patient as he is moved around and can be easily accessed and displayed using an oximeter monitor if the patient transferred to a different room or hospital. During normal operation, when the sensor is plugged into the monitor, the monitor receives the signal from the photo-detector within the sensor and processes this signal to obtain the desired physiological data. In some prior art conventional monitors, the physiological data is stored in a memory within the monitor and retrieved at a later time by a caregiver when requested. However, when a patient is moved to new locations and different monitors are used, the data stored in the monitor at the previous site is typically not available at the current site, and the historical data is unavailable.

In accordance with the present embodiments, the physiological data is processed, displayed, and stored in the monitor in the normal or usual manner. In addition, the data is compressed and provided to the sensor for storage in the memory 236 associated with the sensor. Alternatively, uncompressed data can be provided to and stored in the memory 236. When the sensor is later plugged into another monitor, the new monitor can retrieve the data stored in the sensor memory, decompress the retrieved data, and display the decompressed data. In an embodiment, when the sensor is first plugged into a new monitor, the monitor retrieves and displays the historical physiological data for the most recent predetermined period (i.e., the last 20 or 30 minutes). This predetermined period can be programmed by the clinician or can be preprogrammed into the sensor memory.

Alternatively, the monitor can be configured to retrieve and display the historical physiological data at any time upon request by a health care giver (or a clinician), by the health care giver simply activating a control knob on the monitor. The monitor can be preset so as to automatically retrieve the data upon occurrence of a predetermined event, such as a sensor being plugged into the monitor, or can be preconfigured so that the data is only retrieved upon explicit command by a health care giver.

The pulse oximeter can keep track of how long a particular patient has been monitored by the pulse oximeter and can periodically store that time interval in memory 236 by checking the elapsed time on a counter. For example, a time stamp of the data can be stored. In this case, the first data sample includes the specific time (e.g., date and time) when the data is recorded. Subsequent data samples can be indicated by the number of epochs away from the first (or a previous) data sample. The counter may be a circuit element in the oximeter monitor that is reset each time the oximeter monitor begins to receive data signals from a sensor or each time that the oximeter monitor is turned off. The time period that a patient has been monitored by the oximeter sensor may be displayed on a display screen for viewing.

The pulse oximeter monitor may also include a digital clock that keeps track of the current date and time. The date and time that the oximeter monitor was turned on and the date and time that the oximeter monitor was turned off may be encoded into the sensor in memory 236. When the oximeter monitor is turned back on again, the monitor can display the date and time that it was last turned on and off. It may be desirable for medical personnel to know the last time that patient's vital signs were monitored by the oximeter. The sensor memory can also store an indication of a disconnection of the sensor from the monitor. This data allows the clinician or medical personnel to delineate the events retrieved from the sensor memory.

The oximeter monitor instrument may also write the alarm limits used with a particular patient into memory chip 236. Alarm limits are values that represent maximum or minimum values of patient trending data tracked by the oximeter (such as blood oxygen saturation, pulse rate, pulse amplitude, etc.) that will trigger an alarm, because they are considered to be dangerous levels. The alarm limit values may be encoded in memory 236 by the manufacturer or by a clinician through the oximeter monitor prior to operation.

The oximeter monitor periodically checks the patient's monitored trending data against the alarm limit values. When one of the monitored patient parameters reaches the alarm limit value stored in memory 236, the oximeter monitor triggers an alarm which alerts medical personnel that a problem may exist. Present embodiments also allow patient-specific alarm values to be set by medical personnel through the oximeter and stored in memory 236 so that as the patient moves from monitor-to-monitor (while the sensor stays with the patient), the appropriate alarm limits need not be reset each time on the new monitor. Instead, the alarm limits only need to be programmed once, or at a later time, whenever the clinician adjusts alarm limits.

One or more of the patient trending data including blood oxygen saturation, pulse rate, and pulse amplitude can be written to memory 236 along with a time of occurrence whenever an alarm threshold is crossed. Additional information, such as the readings for a predetermined time prior to an alarm occurrence can also be stored, and/or periodic values during the alarm breach can also be stored in memory 236.

Currently sensors are placed on patients at one hospital site and stay with the patient from hospital site-to-site. It would therefore be desirable to have a patient identification code (patient ID) such as a unique number carried along in the sensor so that the record keeping, which occurs at each site, can link the recorded information with the patient. Without a patient ID stored in the sensor itself, the tracking has to be done manually.

Thus, in a further embodiment, the oximeter monitor can store a patient ID in memory 236 of sensor 130. The oximeter has an input device such as a keyboard, touch screen, or scanner that allows a patient ID to be entered and reentered into the oximeter so that it can be stored in sensor memory 236. With patient trending information being stored in memory 236 of the sensor 130 as discussed above, it is also desirable to have the patient ID stored in memory 236 so that as the patient goes from hospital location to location, the new location's staff can verify that old trending information stored in memory 236 was indeed obtained from that particular patient. Medical personnel can check that the patient ID stored in sensor 130 matches the patient ID on the patient's chart and other paper documentation to verify that these medical records correspond to the correct patient. If desired, the oximeter sensor can be interfaced with a hospital computer network that maintains a database of patient ID numbers to verify the identity of the patient and to obtain medical records and other information for the patient stored on hospital databases. The patient ID stored in memory 236 provides assurance that any data read from memory 236 of the sensor is correlated with the patient they are receiving.

The pulse amplitude of the measured photoplethysmogram is an indirect measure of blood perfusion (flow) in the local tissue, changes in blood pressure, vascular tone, vasoconstriction or dilation, for example, all have an effect on the pulsatile signal strength observed with a pulse oximeter. The measured modulation, or other measurement of perfusion, can be stored in memory 236 for patient trending purposes. The oximeter can compare current modulation and perfusion data with older data from memory 236 to determine patient trends over time. The patient's pulse amplitude deteriorating over time may reflect a serious condition that demands attention. Therefore, it is desirable to store and monitor changes in a patient's perfusion over time. Also, a maximum or minimum perfusion limit may be stored in memory 236 that represents the maximum or minimum value that the patient's measured perfusion can reach before the sensor needs to be moved, repositioned, or adjusted in some other way. The oximeter can trigger a warning signal or light when a perfusion limit has been reached or a significant change has occurred.

The sensor memory can also include a field that indicates when the sensor memory is full. The information in this field can be provided to the monitor to direct the monitor to cease sending data to the sensor memory. The information in this field can be prominently displayed by the monitor to notify the clinician or medical personnel. Also, in response, the monitor can generate an alarm (i.e., blinking light or an audio alarm, or both) to draw the attention of the clinician to the operating state of the sensor.

The sensor memory can also store data for various physiological characteristics such as, for example, heart rate, blood pressure, temperature, and so on. For example, the sensor memory can be used to store NIBP, IBP, and ECG waveforms. Moreover, as memory costs continue to fall and larger memories become available, more complex physiological parameters can be measured and stored.

Additionally, information about the monitor can be stored or embedded along with the physiological data. This additional information may include, for example, the serial number of the monitor to which the sensor couples, the sensor connect/disconnect times, monitor diagnostics, and others. This information would allow the clinician to access historical information on the instrument as well as the physiological data, which might be useful, for example, in product liability and malpractice litigation or in troubleshooting instrument performance questions.

The memory 236 associated with the sensor can be physically located in a variety of places. First, it can be located on the body of the sensor, in a vicinity of the photodetector, LEDs, or other sensor components. Or, the memory can be in the sensor connecting cable 124 or the sensor connecting plug 122, or in an adapter module that connects to a front of an oximeter, to an oximeter cable, or to a sensor plug or cable. Whether or not the memory 236 is in the sensor body, sensor cable 124, sensor plug 122, or adapter module, it is always "associated with" the sensor since the memory travels with the sensor and patient when the patient is moved and the sensor is disconnected from the monitor.

The monitor and sensor can be configured such that the data is provided to and stored in the memory 236 automatically and continuously. The monitor and sensor also employ automated event recording, such that the monitor in response to an oxygen desaturation event transfers some of the physiological data to the sensor memory. Alternatively, particularly when a size of the memory is small, the monitor can require a user first command the monitor (e.g., by activating a control knob) to send data to the memory 236. In this case, valuable storage space in the memory 236 will only be used (and consumed) when the patient being monitored is believed to be relatively unstable by the caregiver and when it is believed storage of the historical data for later retrieval may be particularly desirable.

As noted above, the techniques can be used to store and provide various physiological data including, but not limited to, blood oxygen saturation, heart rate, temperature, and blood pressure data. For clarity, the invention is described in the context of the storage and retrieval of blood oxygen saturation ($SpO_2$) data. Based on the received signals representative of the intensity of the light detected by photo-detector 240, processor 262 estimates oxygen saturation using algorithms that are known in the art.

The saturation data for a particular patient is processed by the monitor attached to the sensor, and the processed data is provided to the sensor for storage in the sensor memory. The selection of the sensor memory is dependent on numerous factors including cost, the amount of data that needs to be stored for a particular application, the amount of achievable data compression (if compression is used), the physical dimensions, and so on. For oxygen saturation, storage of approximately one to seven days of historical data is adequate for many applications.

In an embodiment, to reduce the amount of data to be stored in the sensor memory, the physiological data is compressed before storage. In an embodiment, the compression is performed by facilities located within the monitor. Alternatively, the compression encoding circuit can be on the sensor itself. The monitor further includes facilities to decompress the data later retrieved from the sensor memory. Compression allows for the use of a smaller-sized memory in the sensor. This is particularly advantageous in the case of single patient use disposable sensors which are typically disposed after use on a patient. Compression also allows more data to be stored into a memory of a given size. The ability to store a large amount of data is important for many diagnostic applications that require data collected over hours or days.

The compression scheme can be designed to take advantage of known characteristics of the physiological data being stored. For example, it is known that oxygen saturation generally does not change rapidly. This characteristic can be exploited to achieve significant compression, as described below.

For arterial oxygen saturation data, one compression scheme is based on the realization that saturation data generally exists in two dimensions, time and absolute saturation value. Saturation sample time is about one hertz normally, assuming one saturation value is determined by a monitor for each patient heartbeat. The number of possible saturation values generally corresponds to 101 possibilities, which assumes each possibility corresponds to an integer saturation percentage which must lie somewhere between 0% to 100%. A goal is to use a compression coding technique which reduces the scope of these two dimensions, which again are 1 Hz by 101 saturation values, to a smaller region, e.g., 0.1 Hz by 8 saturation values, for example, and yet retain the usefulness of the information. According to one embodiment, Huffman compression is used with run length encoding, or alternatively or additionally differential encoding.

Run length encoding simply means that if the same saturation value is to be repetitively transmitted, rather than repetitively transmitting this value, it can be more efficient to count the number of consecutive times the value occurs, and to instead transmit the value and the number of times it is repeated. Differential encoding, though similar, is different in that a difference between consecutive saturation values to be transmitted is calculated, and along with the original saturation value one transmits the differential between adjacent values and the number of times an identical differential occurs. There are many known permutations of these two types of common compression techniques known in the art.

As noted above, if saturation percentages were to be reduced to a group of eight values, any single value would correspond to a range of saturation percentages. For example, ten values could be selected, with each value corresponding to an incremental increase of 10 saturation percentage points. A disadvantage of such a grouping is that a patient who has a saturation which is toggling between groups by only one saturation percentage, e.g., toggling between 89% and 90%, can require a great deal of memory to record this information since the advantages of run length encoding are greatly diminished if the identity of the group is repetitively changing.

Accordingly, it has been determined that it may be desirable to utilize saturation values which have saturation percentages which overlap. For example, eight saturation values could be as follows:

| Saturation Value # | Saturation Range (%) |
| --- | --- |
| 1 | 85-100 |
| 2 | 80-90 |
| 3 | 75-84 |
| 4 | 70-79 |
| 5 | 65-74 |
| 6 | 60-69 |
| 7 | 1-64 |
| 8 | 0 |

Since these saturation values have saturation percentages which overlap, toggling at a boundary between values 1 and 2 is prevented for small saturation changes. For example, if value 2 has previously been stored based on a saturation of 90%, and the saturation moves to 91%, the saturation range will now correspond to value 1, and this value will be maintained until the patient saturation falls below 85%. Hence, with overlapping values or groups, it is readily apparent the advantages of run length encoding will be more readily achieved for all patients except the most unstable whose saturation varies by relatively large amounts in relatively short periods of time.

Turning to the other dimension involved with saturation, specifically saturation sampling frequency, for a sampling rate of 0.1 Hz, a single saturation value can be determined for a patient based upon their average saturation every 10 seconds. Lower sampling frequencies could be used which generate less data, which consume less memory, but a disadvantage is that correspondingly less information will be stored in the memory. Conversely, higher sampling frequencies could be used which result in more information being stored in the memory, with a corresponding disadvantage that more memory is required.

Regardless of the saturation sampling frequency, and the number of saturation values or groups which are used, further compression can be achieved by overlaying Huffman encoding techniques, which simply means that if a mean value to be transmitted is relatively high, such as 95, this value can be normalized to 0 using Huffman encoding techniques with the result that fewer bits are required to transmit relatively large numbers by such normalization.

Several compression embodiments have been described for oxygen saturation data. Although present embodiments can be practiced without the use of compression, additional capabilities are provided by the judicious use of compression. As used herein, compression includes any processing that alters, however slightly, the original form of the physiological data as they are generated (in the nominal manner) by the monitor. Other compression schemes can also be used and are within the scope of the invention. Of course, no compression could be used.

As noted above, in a specific embodiment, the sensor memory is implemented as a write-once memory device. A field in the sensor memory can be set when the sensor is reprocessed so that the monitor can determine that it is coupled to a reprocessed sensor. The monitor can use the information in this field to disable the display of the historical data (for example, if the memory is write once and relatively full). Alternatively, if the memory is erasable, a field for storing historical physiological data could be erased during sensor reprocessing.

Disabling the data display may be preferable in some applications to ensure the integrity of the collected data. For a memory device that can be written once and has a fixed memory size, it may not be possible to determine where the "old" data came from or how much memory may still be available on a reprocessed sensor. Moreover, it is highly desirable to avoid having data from an old patient being displayed and potentially mistaken as valid data for the patient to which the sensor couples. Since it is not easy to control or determine the amount of available unwritten memory after a use, which can vary from zero to the full amount, inconsistency and potential customer dissatisfaction may result from using a sensor having widely varying amounts of available memory. By not displaying data from reprocessed sensors, these potential problems are avoided.

Embodiments may provide advantages not available in conventional monitors and sensors. For example, certain present embodiments allow for monitoring of a patient in transit who may be connected to two or more monitors over a period of time. One such situation is a patient who is transported in an ambulance to an emergency room and later transferred to an intensive care unit. This technique is especially beneficial in this application since this particular patient is more likely to be in need of close monitoring and recent historical physiological information.

Present embodiments can also be used to document physiological characteristics. For example, for a patient in home care who requires oxygen, documentation of oxygen saturation is typically needed. In this case, the sensor of the invention can be used to store saturation data for the patient over a predetermined time period (i.e., one week). At the end of this period, the caregiver can simply remove the sensor and send it away as documentation of the patient's saturation. These techniques can also be used to collect data for other applications such as, for example, sleep diagnostics, de-saturation, and so on.

The sensor in accordance with present embodiments has been described for use in combination with a monitor that performs the signal processing of the detected signal and compression of the processed data. In another embodiment, the sensor of the invention includes the facility to process (and compress, if necessary or desirable) the detected signal. This embodiment advantageously allows for independent operation of the sensor without support from a monitor. The data stored within the sensor can be provided to a monitor for display. The amount of signal processing and compression that can be achieved by circuitry within the sensor is only limited by the available technology, which inevitably improves over time. In the near term, physiological data that does not require extensive signal processing and compression (e.g., temperature, peak amplitude in a waveform, heart rate, and so on) can be collected and stored by the sensor.

Figure 3:
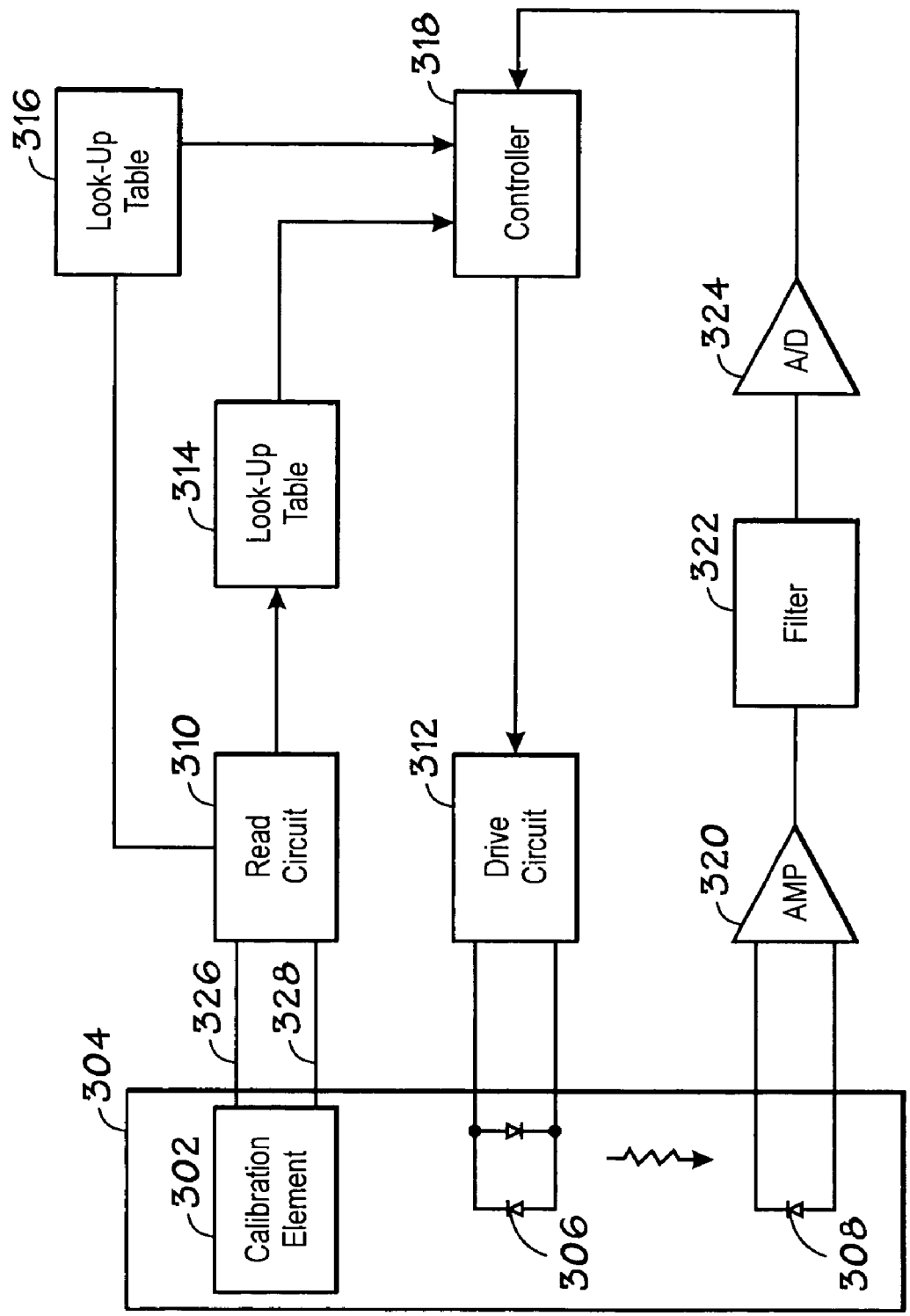
FIG. 3 shows a block diagram of a pulse oximeter system incorporating an exemplary calibration memory element according to an embodiment.

FIG. 3 is a block diagram of a pulse oximeter system incorporating a calibration memory element 302 in accordance with embodiments of the present invention. In one embodiment, memory element 302 is a two-lead semiconductor digital memory chip. The calibration element 302 is part of a sensor 304 which also includes red and infrared LEDs 306, along with a detector 308. If desired, LEDs 304 may be replaced with other light emitting elements such as lasers.

The oximeter includes read circuit 310, drive circuit 312, look-up tables 314 and 316, controller 318, amplifier 320, filter 322, and analog-to-digital converter 324. Read circuit 310 is provided for reading multiple coded values across the two leads 326, 328 connected to calibration element 302. One value is provided to a look-up table 314 to determine appropriate wavelength dependent coefficients for the oxygen calculation. The other value(s) are then provided to another look up table(s) 316 which provides input (e.g., coefficients) to other calculations performed by controller 318. These additional calculations may enhance the performance and/or safety of the system. Controller 318 provides signals to a drive circuit 312, to control the amount of drive current provided to LEDs 306.

Detector 308 is connected through the amplifier 320 and the filter 322 to the A/D converter 324. This forms a feedback path used by controller 318 to adjust the drive current to optimize the intensity range of the signal received. For proper operation the signal must be within the analog range of the circuits employed. The signal should also be well within the range of A/D converter 324. For example, one rule that may be applied is to adjust LED drives and amplifier gains so that both red and IR signals fall between 40% and 80% of full scale reading of converter 324. This requires correct and independent settings for both the red and infrared LEDs.

Part II

Embodiments of the present technique include the following:

Sensor Model ID

Encoded text of the specific model of sensor would allow the instrument to display a text string indicating what sensor is being used, e.g. "Nellcor OXISENSOR II D-25" or "Adult Digit Sensor" or "Agilent N-25". Alternately, a sensor code could be stored that points to a lookup table of display text. Encoding sensor model ID could also be used to accommodate sensor-specific operating parameters such as LED drive currents or "sensor off" characteristics (as an alternative to programming the value of drive current or "off" characteristics themselves).

Sensor Model—Specific Information

Coefficients for Taylor's Series Calibration Curves

The sensor may store a general polynomial curve. Other families of polynomials, such as Tchebyschev polynomials, could be used as well. This may also pertain to other calibration information, such as temperature calibration and force transducer calibration. This allows new sensor types (such as a sensor with an offset emitter and detector).

Sensor Adjustment/re-application Light Levels
Sensor Off Light Levels

Under normal operating conditions, photosignals coming from the sensor LEDs generally fall within a certain range. When a sensor is removed from a patient, or falls off on its own, the photosignal usually changes. This is particularly true for the reusable clip-style sensor, since in their normal disconnected state, the LEDs shine directly onto the photodetector unimpeded by, for example, tissue. By programming a "threshold photocurrent" into the memory chip, reliable detection of a "sensor is off the patient" condition can be accomplished (in this example, exceeding a certain detected light level is a sure sign the sensor is not on a finger or other opposed site). For certain other sensors, a low light level may be indicative of the sensor being off (an adhesive sensor, for example, lays flat when in its natural state, so little LED light may reach the detector). Encoding an expected range of light levels for the specific model of sensor being used allows enhanced detection of when the sensor is improperly placed or has been removed.

Temperature at which to Switch to STORM Algorithm

The STORM algorithm here refers to the sensors designed to be used where "motion provides the signal", i.e., the cardiac pulse need not be present or discernible in order for the oximeter to provide $SpO_2$ values. Instead, the red and IR waveforms resulting from the motion itself are used for determining the arterial saturation. This feature is possible for tissue beds that are well "arterialized" (a large supply of arterial blood relative to the metabolic needs of the tissue) resulting in a small aterio-venous saturation difference, as well as other signal characteristics that are not germane to this discussion. It has been observed that the necessary degree of arterialization correlates well to being "well perfused" at the tissue site, which itself correlates well to the tissue bed being warm. Thus by monitoring the temperature of the skin at the sensor site, and by knowing a value of temperature (programmed into the memory chip) at which the "motion-is-signal" algorithm can be utilized for the specific sensor design being used, improved reading accuracy through motion can be better accomplished.

Additional Information on Use of Pins
Contact Switch—Sensor Off

Similar to the contact electrodes of the Nellcor FS-14 fetal sensor, an extrinsic probe of skin contact can be used to indicate whether the sensor is in adequate contact to the patient. This extrinsic probe could be accomplished, for example, through an impedance measurement across two electrodes, a force or pressure switch that is sensitive to whether adequate force or pressure is present in the sensor placement, or through other means. Dedicated sensor connector pins, or pin-sharing, could be used to accomplish this additional measure of sensor-patient contact.

Chemical Sensor for EtO Cycles

An electro-chemical or thermal device that senses and stores to memory the number of exposures (zero, once, or potentially more than once or the actual number) to sterilization cycles could be used to capture the history of the sensor. Excessive exposure to sterilization cycles degrades a number of components in the sensor, and can affect its performance. A sensor exceeding a certain number of exposures could cause a display to indicate the sensor needs to be replaced.

Sensor Expiration

This need not be a separate device, but the memory could contain a date after which time the sterilization can no longer be certified as being effective. Sterilization can be sensed and the date recorded automatically by the sensor itself.

Sensor Expiration Date/Sensor Parking: Meter

At the time of manufacture, the expiration date of the sensor may be written into the memory chip. The memory-enabled instrument would then do something with this knowledge (e.g., indicate "expired sensor", or refuse to function if expired). Alternately, the elapsed time of sensor usage could be tracked in the memory chip (written to it by the instrument) and the sensor would "expire" after a memory programmed maximum (greater for reusable sensors than for single-use sensors).

Auto Shut-Off

After sensor expiration, the instrument may refuse to function with this sensor and would indicate that a fresh sensor is needed. Furthermore, the sensor could be disabled by running a high current through it, or by other means.

Warranty Date

Similar to the expiration date, the date of expiration of the sensor warranty could be written into the memory chip (e.g., 2, or 6, or 12, etc. months from the date of 10 manufacture or the date of first use). The instrument would give some indication of this as appropriate.

Patient Specific Information (Written to Sensor from Monitor)

Trending and/or data logging of patient monitoring parameters may be stored in the memory of the memory chip. As the patient and sensor travel from ward-to-ward of the hospital, and consequently plug into different oximeters, the patient-specific data could be displayed as it is contained in the patient's dedicated sensor. Examples of the type of data are given below:

Trending
Low High Sat

The lowest and/or highest $SpO_2$ value during the monitored time, or the lowest/highest values over the past specified monitoring time (e.g., 2 hours, 1 day, etc.)

Duration of Monitoring

How long has the patient been monitored by the pulse oximeter? (elapsed time counter).

Beginning and End of Monitoring

Clock time of when the monitor was turned on and off.

Pre-Set Alarm Limits

The alarm limits used with this patient become written to the memory chip by the instrument. This allows patient-specific alarm values to be set and memorized so that as the patient moves from monitor-to monitor (the sensor staying with the patient), the appropriate alarm limits need not be reset each time on the new monitor. Instead, this only needs to happen once, or whenever the clinician adjusts alarm limits.

Changeable Key

Data encryption utilizes private and/or public keys to scramble the data written to the memory chip and later decipher the data so that only authorized devices are supported. To further prevent the use with a monitor that is not certified to provide correct results, the sensor manufacturing system could periodically change the private and/or public keys. The change in the key could be communicated to the instrument via the memory chip in encrypted form. The purpose of this feature is to elevate the level of security in the memory system.

Monitor Code Upgrades from Modem or Sensor

Distributing code updates in memory. Whenever an oximeter notes that a code update field is present in the sensor, it would check whether the proposed update had previously been installed, and (if not) whether any indicated prerequisites were present (e.g. a code patch might not function properly in the absence of a previously-circulated patch): If appropriate conditions are met, the code upgrade would be installed. If prerequisites are missing, a message would be displayed to the user, telling him how to obtain the prerequisites (e.g. call Nellcor).

Black Box Encoder (Patient History, Serial Number of Box. etc.)

Use the memory as a general-purpose carrier of patient data, covering not just oximetry but a lot of other information about the patient.

Optical Efficiency Correction

If it is desirable to know where a particular patient lies in COP space, it is useful to know the inherent brightness of LEDs, sensitivity of detector, and anything else about the particular sensor assembly (e.g. bandage color and alignment) that will affect the amount of light which the sensor receives. Given that information, a measure of the patient's optical transmissivity may be computed for each LED wavelength, which depends almost entirely on the properties of the patient. Signal to noise ratio of the oximeter is probably determined by the size of the detected signal, not by the transmissivity of the patient alone. This could take advantage of DC transmissivity of the tissue to improve the accuracy of pulse oximetry.

Another reason for recording LED and detector parameters in the sensor memory is to provide a basis for later research on the drift of these parameters due to various environmental conditions which the sensor experiences. Parameters of interest include not only LED power and detector sensitivity, but also LED wavelengths, FWHM, and secondary emission level.

Pigment Adjustment Feature

For some types of sensors, the accuracy of the sensor may be different for patients with different skin color. The sensitivity of accuracy to skin color may depend on sensor model. The sensor might contain a sensitivity index, indicating how large an adjustment in readings should be made as a function of skin color. Skin color might be obtained by user entry of the data (e.g. menu selection). Another option would be for the sensor to measure skin color. One way to achieve the latter option would be to provide transmission sensors with auxiliary detector for "reflected" light. In combination with the optical efficiency information noted above, the signal levels reported by the auxiliary detector would sense to what extent the patient's skin was affecting red and IR pathlengths differently, and hence to what extent readings needed to be corrected.

Accelerometer on Chip

This might be used in a scheme in which the memory chip was on the bandage, not in the connector. This combines a MEMS accelerometer with any of several different chips that might usefully be placed in the sensor head, local digitizing chip, preamp chip, memory chip.

Accelerometer data may be used to warn of the presence of motion (in which case special algorithms may be called into play or oximetry may be suspended), or actually to help correct for motion (to the extent to which we can produce algorithms which can predict physio-optic effects of known motion).

Optical Shunt

The amount of optical shunting could be measured for each sensor, or family of sensors. The value or values of which would be stored in the sensory memory for the monitor to read and use to adjust the processing coefficients.

Monitor Chip Temperature

The temperature of a red LED, in particular, affects its principal wavelength, which affects calibration. For one class of LEDs, the wavelength shifts by about 0.14 nm/C. The memory chip might contain circuitry capable of monitoring a thermistor or thermocouple, or the memory chip could be mounted in proximity to the LED (e.g. under it), so that it could sense directly the temperature of the LED, and provide a calibration correction accordingly.

Monitor Ambient Temperature

This might be used, e.g., in overseeing the operation of a warmed ear sensor. There is a thermal cutout in the control system of the WES, that causes operation to terminate if the sensor goes over a certain temperature. This is a component for protecting the patient against burns. If the reason for a high sensor temperature is that the environment is warm, it could be quite acceptable to continue oximetry, even though warmer operation would be shut down. In the absence of knowledge about environmental temperature, a high temperature reading might have to be assumed to mean that something was wrong with the sensor, in which case all operation might have to cease. An environmental temperature sensor in the plug could help to tell which rule to apply. Again, the memory chip could record the calibration of whatever device was used for thermometry.

A passive component on the memory chip could be the thermometric sensor, and a resistance or voltage measuring device in the instrument could read out that sensor. Thus, ambient temperature sensing might not require that large changes be made in the memory chip.

Temperature Amplifier/Detector

In illuminating the skin for the purpose of making oxygen saturation measurements, some heat is generated by the LED emitters. Tests have been done to establish the maximum safe current for the LED drive which will assure that the skin temperature stays within a safe value for the worst case sensor/patient conditions. This means that in all cases the sensor will be operated at cooler than the maximum temperature but in most cases well below the maximum temperature.

To establish the optimum signal for the measurement, it is desirable to drive the LEDs with higher current than is imposed by the above limitations. The temperature amplifier/detector would allow the LEDs to be driven to a level that still results in a safe temperature by monitoring the temperature, yet in many cases allow more drive current, and therefore higher signals, which could give better readings.

The inexpensive thermistor devices that could be used in this application are characterized to allow the measurement to be accurate. These characterization values could be stored in the sensor where the thermistor is located. While in operation, the oximeter would be able to read the characterization values from the sensor, measure the resistance of the thermistor, and calculate accurately the temperature of the skin surface where the thermistor is located. This would keep the patient safe from burns and still provide the best signal available.

RCAL Resistance Built into Chip

In legacy oximetry sensors there is a resistor which is selected and installed in the sensor connector, to correspond to the wavelength of the red LED. The wavelength difference from LED to LED has an impact on the calibration of the saturation measurement, if not compensated for. The oximeter will read the value of resistance and adjust its calculation accordingly.

When adding the memory chip, memory compatible oximeters will be able to obtain the necessary calibration coefficients from the memory chip but the legacy instruments will still need a calibration resistor value. If the resistance were built-in to the chip and trimmed or selected at manufacture then only one device would need to be installed in the sensor connector. That would reduce the overall cost, yet keep the sensor compatible with both the legacy instruments and the new memory compatible instruments.

Secondary Emission Measurement

The oximeter is measuring the relative transmission of the red and infrared light through the tissue. LEDs have a characteristic called secondary emission which is indicative of the amount of light, at wavelengths other than the primary wavelength, that is being emitted. This characteristic will change the calibration of the device if not compensated for. It is possible to make an oximeter that will function within calibration if the secondary emission is known and compensated for. If the LED were characterized during manufacture and then the secondary emission values entered into the memory chip, the oximeter would be able to read those values and compensate for them so that the sensor was used properly. This would increase the range of LEDs that could be used for oximetry, reduce cost and provide better calibration across a wider range of LED emitters.

Patient ID (Potentially as Tracking Device, Archiving Patient History etc.)

Currently sensors are placed on patients at one hospital site and stay with the patient from hospital site-to-site. It would be helpful to have the patient ID carried along in the sensor so that the record keeping, which occurs at each site, would be able to link the recorded information with the patient. Without patient ID, the tracking has to be done manually. With trend information being stored in the sensor it also would be desirable to have the patient ID included so that as the patient went from location to location, the new location's staff could verify old information and be assured that it correlated with the patient they were receiving.

Encode Contact Resistance (e.g. for Oxicliq)

When making measurements of the resistance that is placed in the sensor for calibration information purposes, one of the factors that can influence that measurement is the contact resistance of the connectors that are between the oximeter and the resistor itself. In order to compensate for connectors that are significant in their impact on the measure, one could encode the contact resistance of the connector and subtract that algorithmically from the measured resistance to get a more accurate measurement of the resistance of the calibration resistor. This would enhance the accuracy with which the resistance measurement is made and, therefore, make the instrument less prone to inaccuracies in saturation calculation and display.

Measure Capacitance to Balance Common Mode Rejection

One of the interfering noise sources that plagues oximetry is that of common mode noise. This can come from the surrounding electrical environment. Other instruments, lighters, drills etc. can produce electrical fields that can couple into the cable between the patient and the oximeter. Once coupled-in, they can make measurements more difficult, less accurate, or not possible, depending on the severity of the noise. To help reduce this common mode noise, differential amplifiers are used for amplifying the signal from the sensor. These amplifiers amplify only the difference between two signal wires. Thus, if the common mode signal is coupled exactly the same into both wires, the amplifier will not amplify it because the same signal is present on both wires.

If the two wires have different coupling to their electrical environment, then they will present different signals, and the difference will be amplified as if it were a signal. One component that influences this coupling is the capacitance of the lines to the outside world. This is affected by the manufacture of the cable, materials, twists in the wire, etc. If one measured the cables during manufacture and then stored that information in the memory chip, it could be read when the oximeter is operating. Once the capacitances for the two wires to the shield are known, the instrument could be provided with a tunable capacitance device that would then balance the two lines again and make the noise coupling to the lines better matched. This would reduce the amount of susceptibility to the external noise that got coupled into the patient cable. Reduced noise results in better measurements or the ability to make measurements at all on some patients.

Fiber-Optic Infrared Wavelength Shift

The relative wavelengths of the red and infrared light that is used to make the measurement in oximetry are important to know so that calibration can be maintained. In traditional LED oximetry, the LED sources are at the skin so that whatever wavelength is emitted is what is sensed by the photodiode that receives the light. The red LED is the only one that we need to characterize for accurate saturation measurements to be realized. The saturation is less sensitive to the IR wavelength as long as it stays fixed in the acceptable range that has been specified for the IR LEDs.

When using plastic fibers for transmission of the light, there is a wavelength dependent absorption caused by the fiber. This has the effect of altering the apparent center wavelength of the IR source, which can affect calibration of the unit. By characterizing the fiber for its shift, one could then provide the proper compensation in the algorithm that calculated the saturation. This would restore the accuracy that would otherwise be lost in fiber transmission of the light.

Inform Monitor of Extra LEDs

There are limitations on the number and type of blood constituents that can be sensed using the two conventional LED wavelengths of the oximeter. The accuracy of the oximetry measurement can also be improved by using different wavelengths at different saturation ranges. An analysis unit could be developed that would utilize either or both of these features. To do this, it would be able to drive additional LEDs. The additional LEDs could be driven along with the traditional ones or separately. The oximeter (or additional constituent measurement unit) would provide the capability to calculate values for these other wavelengths, and the sensor would provide the additional information to allow the oximeter to make that calculation. These could be stored in the memory.

Active Ambient Light Measurement

One of the problems with oximetry sensors is the interference caused by ambient light in the environment. This can be made worse when a sensor comes loose or when the ambient light is extremely high in value. By characterizing the sensor, one could know what level of ambient light could be expected or tolerated, and give a warning to the user when the level has been exceeded. This would give them the opportunity to adjust the sensor, the light, or both to affect an improvement in the performance of the oximeter.

Active Pressure Adjustment for Modulation Enhancement

The stronger the pulsatile signal, the better the chances are of measuring the saturation accurately. One way to enhance the modulation percentage is to apply pressure in the range of the median pulsatile pressure. If this were implemented, one could use relatively low cost transducers and supply calibration coefficients in the memory to allow accurate pressure readings to be made. The memory could also contain the pressure settings and/or expected modulation enhancement capability to determine effectiveness of the pressure enhancement.

Measure Perfusion

The amount of perfusion affects the amount of modulation, and thus the AC signal. This affects both the percentage of modulation vs. the DC amount, and the absolute size of the modulation. The measured modulation, or other measurement of perfusion, can be stored in memory for trending or setting limits on acceptable perfusion before movement or other adjustment of the sensor is required.

Keep Track of Last Time Sensor Moved or Disconnected

The time of movement or disconnecting of the sensor could be written into the memory. Disconnecting can be detected from the interruption of the signal to the monitor. Moving can be detected by a sensor off detection, and a subsequent sensor on detection. Alternately, aggressive movement could be detected and interpreted as moving of the sensor, or a combination with a sensor off detection could be used.

Identify Private Label Sensors

A code can be stored in the sensor memory identifying the sensor manufacturer. This code can be read and used to indicate operability with monitors of other manufacturers, or to indicate any conversion algorithm that may be needed for a signal from a sensor to be used by a monitor from a different manufacturer. The code can also be used to allow only supported features to be used.

Measure Sensor Wetness

A moisture sensor or impedance sensor can detect the amount of wetness of the sensor. This can be used for different purposes and can be stored in the sensor memory for trending or monitoring. To determine sensor malfunction, the sensor can be disabled if the wetness exceeds a threshold, which could be stored in the sensor memory. Some sensors may not provide for isolation of the patient from the electronics for excessive wetness. The maximum allowable wetness could be stored in the sensor memory.

Sensor Isolation Indicator

The sensor memory could identify that the sensor provides isolation, so wetness is not a concern. Alternately, it could indicate that isolation is not provided by the sensor, or a limited amount of isolation is provided.

Low Power Mode Identifier (Sensor Tells Oximeter to Sleep or Wake Up)

A portable battery-powered monitor can power down when the saturation is at a good level, and the patient is stable. Minimal circuitry in the sensor could be used to do sufficient processing to tell the monitor when to wake up.

Battery to Run Digital Chip

A battery can be included in the sensor for a wireless connection to a monitor. Alternately, a battery could be used to continue to send data when the monitor is powered down.

Motion Generator ("Thumper")

The sensor can include a cuff (which inflates and deflates) or other mechanical mechanism for inducting motion to get a signal or for inducing pulsitile blood flow to improve the signal.

Sensor Force Indicator (e.g., Too Tight)

A transducer can measure the amount of force on the sensor. This can be compared to a maximum value stored in the sensor memory to determine if the sensor is on too tight. The tightness can also be recorded and monitored. For example, a patient could swell, and this could be determined from the trend information and provided as information to a clinician on a display.

Force Transducer Calibration to Get Pressure

A calibration value can be stored in the sensor memory for converting a force measurement into a pressure measurement. A force transducer can then be used to measure pressure.

Number of Wavelengths

The sensor memory can store an indication of the number of wavelengths used in the sensor, and could store the wavelengths themselves.

Drive Information

The sensor memory can store information about when to drive which LEDs. They could all be driven at once, or a subset could be driven, for example.

Display for Additional Wavelengths

The memory can store information about what parameters are to be analyzed and displayed when the extra wavelengths are used. Oxygen saturation may be displayed when 2 wavelengths are used, while additional information could be displayed when an extra wavelength or more are used (Hct, COHb, etc.).

Recycling Times

Each time a sensor is recycled (sterilized and reconstructed), a number in the sensor memory can be incremented. This can be used to prevent operation of the sensor if it has been recycled more than the allowed number of times (e.g., 3 times).

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth. Therefore, many modifications may be made to adapt a particular situation or material to the teachings of the invention without departing from the essential scope and spirit of the present invention. It is intended that the invention not be limited to the particular embodiments disclosed, but that the invention will include all embodiments and equivalents falling within the scope of the claims.

What is claimed is:

1. An oximeter system, comprising:
  an oximeter sensor, comprising:
    a light emitting element configured to emit light;
    a light detector configured to detect the light; and
    a memory storing an optical shunting measurement for the oximeter sensor; and
  an oximeter monitor, comprising:
    a drive circuit configured to provide signals to circuitry of the oximeter sensor; and
    a receiving circuit configured to receive data including the optical shunting measurement from the oximeter sensor, wherein the optical shunting measurement facilitates adjustment of a processing coefficient.

2. The system of claim 1, comprising a plurality of optical shunting measurements stored in the memory, the plurality of optical shunting measurements relating to a family of oximeter sensors.

3. An oximeter monitor, comprising:
  a drive circuit configured to provide signals to circuitry of an oximeter sensor;
  a circuit configured to receive an optical shunting measurement of the oximeter sensor from a memory of the sensor; and
  an adjustment circuit configured to read processing coefficients from the oximeter sensor and adjust the processing coefficients based on the optical shunting measurement.

4. A method of monitor operation, comprising:
  providing signals to circuitry of an oximeter sensor that is configured to couple to a patient;

receiving information from a memory of the oximeter sensor, the information comprising an optical shunting measurement for the oximeter sensor; and reading processing coefficients from the oximeter sensor and adjusting the processing coefficients based on the optical shunting measurement.

5. The method of claim 4, comprising receiving a plurality of optical shunting measurements for a family of oximeter sensors.

6. An oximeter monitor, comprising:

a drive circuit configured to provide signals to circuitry of an oximeter sensor;

a circuit configured to receive an optical shunting measurement of the oximeter sensor from a memory of the sensor; and an adjustment circuit configured to store processing coefficients and adjust the processing coefficients based on the optical shunting measurement.

7. A method of monitor operation, comprising:

providing signals to circuitry of an oximeter sensor that is configured to couple to a patient;

receiving information from a memory of the oximeter sensor, the information comprising an optical shunting measurement for the oximeter sensor; and storing processing coefficients and adjusting the processing coefficients based on the optical shunting measurement.

8. The method of claim 7, comprising receiving a plurality of optical shunting measurements for a family of oximeter sensors.

* * * * *